(12) United States Patent
Rahbar et al.

(10) Patent No.: US 10,647,617 B2
(45) Date of Patent: May 12, 2020

(54) METHOD FOR ENZYMATIC REPAIR OF CEMENTITIOUS SURFACES

(71) Applicant: Worcester Polytechnic Institute, Worcester, MA (US)

(72) Inventors: Nima Rahbar, Weston, MA (US); Suzanne Frances Scarlata, Worcester, MA (US); Jessica Anne Rosewitz, Westborough, MA (US)

(73) Assignee: Worcester Polytechnic Institute, Worcester, MA (US)

(*) Notice: Subject to any disclaimer, the term of this patent is extended or adjusted under 35 U.S.C. 154(b) by 0 days.

(21) Appl. No.: 15/903,565

(22) Filed: Feb. 23, 2018

(65) Prior Publication Data
US 2018/0244585 A1    Aug. 30, 2018

Related U.S. Application Data

(60) Provisional application No. 62/463,305, filed on Feb. 24, 2017.

(51) Int. Cl.
| | |
|---|---|
| *C04B 41/50* | (2006.01) |
| *C04B 41/65* | (2006.01) |
| *C04B 41/45* | (2006.01) |
| *C12P 3/00* | (2006.01) |
| *C12N 9/88* | (2006.01) |
| *C04B 41/00* | (2006.01) |
| *C04B 111/72* | (2006.01) |
| *C04B 103/00* | (2006.01) |

(52) U.S. Cl.
CPC ........ *C04B 41/5012* (2013.01); *C04B 41/009* (2013.01); *C04B 41/4535* (2013.01); *C04B 41/501* (2013.01); *C04B 41/65* (2013.01); *C12N 9/88* (2013.01); *C12P 3/00* (2013.01); *C04B 2103/0001* (2013.01); *C04B 2111/72* (2013.01); *C12Y 402/01001* (2013.01)

(58) Field of Classification Search
CPC ............ C04B 41/5012; C04B 41/5011; C04B 41/501; C04B 41/4535
See application file for complete search history.

(56) References Cited

U.S. PATENT DOCUMENTS

| | | | | |
|---|---|---|---|---|
| 4,869,621 | A | * | 9/1989 | McLaren ................. B09B 1/00 405/263 |
| 2017/0029689 | A1 | * | 2/2017 | Wilson ................... C09K 8/467 |

FOREIGN PATENT DOCUMENTS

WO    2015/007011 A1    1/2015

OTHER PUBLICATIONS

Im Gyu Kim et al, "Biomineralization-based conversion of carbon dioxide to calcium carbonate using recombinant carbonic anhydrase", Chemosphere, vol. 87, No. 10, Jun. 1, 2012, pp. 1091-1096.

(Continued)

*Primary Examiner* — Michael P Wieczorek
(74) *Attorney, Agent, or Firm* — Armis IP Law, LLC (57) ABSTRACT

An aqueous solution of carbonic anhydrase and calcium chloride is contacted with a cementitious surface defining at least one opening or fissure in the presence of ambient carbon dioxide to thereby cause the calcium chloride and carbon dioxide to react, whereby calcium carbonate precipitate from the solution and seals the opening or fissure.

10 Claims, 6 Drawing Sheets
(4 of 6 Drawing Sheet(s) Filed in Color)

(56) References Cited

OTHER PUBLICATIONS

Achal V et al, "A review of microbial precipitation for sustainable construction", Construction and Building Materials, Elsevier B.V. Netherlands, vol. 93, Sep. 15, 2015, pp. 1224-1235.
Li W et al, "Calcium carbonate precipitation and crystal morphology induced by microbial carbonic anhydrase and other biological factors", Process Biochemistry, Elsevier Ltd, GB, vol. 45, No. 6, Jun. 1, 2010, pp. 1017-1021.
Notification of Transmittal of the International Search Report and the Written Opinion of the International Search Authority, or the Declaration, PCT/US2018/019424, dated May 22, 2018.
Li, W., et al., "Calcite precipitation induced by bacteria and bacterially produced carbonic anhydrase," Current Science 100 (4), 502-508 (Feb. 25, 2011).
Qian, C., et al., "Self-healing of early age cracks in cement-based materials by mineralization of carbonic anhydrase microorganism," Front. Microbiol. 6, 1225, pp. 1-9 (Nov. 2015).
Lafuente, B., Downs, R.T., Yang, H. & Stone, N. (eds Thomas Armbruster & Rosa Micaela Danisi) 1-30 (W. De Gruyter, Berlin, Bermany, 2015), pp. 1-30.
Jonkers, H.M., Thijssen, A., Muyzer, G. & Schlangen, E., "Application of bacteria as self-healing agent for the development of sustainable concrete," Ecological Engineering 36, 230-235 (2010).
Achal, V. and Pan, X., "Characterization of urease and carbonic anhydrase producing bacteria and their role in calcite precipitation," Curr Microbiol (2011) 62:894-902.
ASCE Infrastructure report card (2017); https://www.infrastructurereportcard.org/, pp. 1-9.
Turner, R.K., "Sustainable development and climate change initiatives," Cement and Concrete Research 38, 115-127 (2008).
Akincioglu, A., et al., "Novel sulfamides as potential carbonic anhydrase isoenzymes inhibitors," Bioorganic & Medicinal Chemistry 21, 1379-1385 (2013).
Tarko, L. & Supuran, C.T., "QSAR studies of sulfamate and sulfamide inhibitors targeting human carbonic anhydrase isozymes, I, II, IX and XII," Bioorganic & Medicinal Chemistry 21, 1404-1409 (2013).
Ferry, J.G., "Carbonic anhydrases of anaerobic microbes," Bioorganic & Medicinal Chemistry 21, 1392-1395 (2013).
Alvizo, O., et al., "Directed evolution of an ultrastable carbonic anhydrase for highly efficient carbon capture from flue gas," PNAS 111(46), 16436-16441 (Nov. 2014).
Penders-Van Elk, et al., "Effect of pKa on the kinetics of carbon dioxide absorption in aqueous alkanolamine solutions containing carbonic anhydrase at 298 K," Chemical Engineering Journal 259, 682-691 (Jan. 2015).

\* cited by examiner

| FIG. 8A | FIG. 8B | FIG. 8C | FIG. 8D |
|---|---|---|---|
|  |  |  |  |
|  |  |  |  |
| FIG. 8E | FIG. 8F | FIG. 8G | FIG. 8H |

METHOD FOR ENZYMATIC REPAIR OF CEMENTITIOUS SURFACES

RELATED APPLICATIONS

This application claims the benefit of U.S. Provisional Application No. 62/463,305, filed on Feb. 24, 2017. The entire teachings of the above application are incorporated herein by reference.

BACKGROUND

Fixing decaying infrastructure involves disposing and replacing the existing structures, processes which generate heat and carbon dioxide ($CO_2$). There are economic and environmental advantages to repair rather than replace cracked structures. However, repair is a slow, exothermic process involving agents such as epoxies and microbes, and results in structures with reduced strength and reliability.

Concrete in its many forms is the single most used construction material in the world, and while a comparatively low producer of carbon emissions by itself, the sheer volume constitutes a significant fraction of man-made global carbon emissions (about 1514 million metric tons of $CO_2$ in 2009).[1] A cumulative degradation caused by salts, alkalis, freeze-thaw cycles, carbonation, and physical wear is inevitable. Known repair processes for cracked and damaged concrete typically rely on matching dissimilar materials, such as inorganic calcium-silica-hydrate (C—S—H) compositions with organic petroleum-derived epoxies. Patching and resurfacing success generally relies on artisanal skill, but can, in itself, cause further damage, potentially undermining the process.[2]

One alternative is biocalcification by use of carbonic anhydrase (CA)-producing microbes to fill gaps, cracks and fissures in concrete. CA is a natural enzyme that is found in all living organisms, including humans. The CA enzyme catalyzes the reaction between calcium chloride ($CaCl_2$) and carbon dioxide ($CO_2$) to produce calcium carbonate ($CaCO_3$). Calcium carbonate self-assembles on smooth and fractured cement paste surfaces to produce stable crystal structures that fills cracks with solid precipitate. The CA enzyme can be employed to produce calcium carbonate at a rapid rate. Also, in contrast to other repair materials, such as organic epoxies, calcium carbonate is a material with similar mechanical properties to cement paste and will produce a final product that is indistinguishable from the original fault-free product. This will also substantially avoid stress concentration arising from dissimilarities among repair and substrate compounds. Importantly, CA enzyme-catalyzed calcium carbonate consumes atmospheric carbon dioxide and decomposes without odor or any risk to human health.

However, use of bacteria or microbes to precipitate calcium carbonate typically mandates subsequent sterilization, such as by applying high-pressure steam, or potentially toxic chemicals. Biological non-enzymatic approaches employing microorganisms such as bacterial spores are currently practiced, but such methods typically lack the speed and specificity of the CA enzyme, and a much greater amount of biomaterial must be consumed.

Even so, the use of bacteria and attendant antibiotics to repair concrete structures, such as buildings that are in direct contact with humans, poses health risks. Existence of spores also creates unpleasant odor when not dormant that will always coexist with the structure. Generally, known methods of concrete repair by use of microbial CA creates environmental and occupational hazards. Moreover, calcite growth by use of bacteria or microbes is also quite slow, and repair of large cracks and pores is not pragmatic as it requires an extended period of time. In addition, the process is limited to a certain class of structures because the bacteria typically retreat to a spore stage and persist. These factors essentially make the use of spores as a self-healing agent only viable for a very limited class of structures.

Therefore, there is a need for a method of repairing cracks and fissures in cementitious surfaces that overcomes or minimizes the above-referenced problems.

SUMMARY

The present invention is a method to heal cracked and damaged concrete using the enzyme carbonic anhydrase (CA) in solution. The CA enzyme catalyzes the reaction between calcium chloride ($CaCl_2$) and $CO_2$ to create calcium carbonate ($CaCO_3$) crystals that adhere to concrete structures.

In one embodiment of the invention, the method of sealing a cement paste surface includes the step of contacting at least one opening or fissure of a cementitious surface with an aqueous solution of carbonic anhydrase, calcium chloride, and carbon dioxide, whereby calcium carbonate is formed and precipitates to thereby seal the opening or fissure.

It has been discovered that a carbonic anhydrase solution can be used as a safe and efficient means for the sustainable repair of structural concrete to produce a strong and stable product. Liquid solutions containing trace amounts of the CA enzyme penetrates deep cracks to produce calcium carbonate crystals that bond to hydrated and cured cement. The use of enzyme in solution enables the method to be performed under conditions that are not well-tolerated by other, non-biological or non-catalytic additives. The method of this invention employs ambient $CO_2$ as a reactant source, generates less heat than present methods, and avoids using toxic or bioactive materials. Moreover, it is safe and adds strength to the substrate structure when repaired. The crystals produced are semi-transparent and dense. In practical applications, delivering the enzyme to the sites can be performed in efficient and inexpensive ways since only trace amounts of an aqueous solution of the enzyme can produce large volumes of precipitate crystals. The use of the CA enzyme in solution provides rapid, strong and environmentally safe repair of concrete.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 4A-4C are images of a cement paste surface during deposition of calcium carbonate by an embodiment of a method of the invention.

FIG. 10 is a comparison of normalized compressive strengths of 25 mm cube samples. The intact control samples (n=8) are the baseline, to which those repaired by the enzymatic method (n=2) and those left unrepaired (n=2) are compared. Repaired samples with a 4 mm circular flaw regained 90% of their strength, while those left unrepaired regained 70% of their strength compared to the control samples. Repaired samples with a 10×5 mm vertically-oriented elliptical flaw regained 80% strength, while those left unrepaired regained 60% of their strength compared to control samples. Samples of compression testing along the top row are photographs prior to testing, and along bottom row are photographs of the same samples after testing.

DETAILED DESCRIPTION OF THE INVENTION

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

A description of example embodiments follows.

In one embodiment, the invention is a method of sealing a concrete surface comprising the step of contacting an opening or fissure of a cementitious surface with an aqueous solution of carbonic anhydrase, calcium chloride, and carbon dioxide, whereby calcium carbonate is formed and precipitates to thereby seal the opening or fissure. In one specific embodiment the solution is exposed to an ambient atmosphere that includes carbon dioxide, such as ambient air. The cementitious surface can take forms, and be referenced by names, such as are known in the art, such as that of cement, concrete, or cement paste.

In one embodiment, the pH of the aqueous solution is in a range of between about 3.0 and about 9.5. In another embodiment, the pH is in a range of between about 6.5 and about 9.5.

The molar concentration of carbonic and hydrous of aqueous solution is, in one embodiment, in a range of between about 0.5 μM and about 1 μM. In another embodiment, the molar concentration of carbonic anhydrase of the aqueous solution is in a range of between about 1 μM and about 10 μM.

In another embodiment, the molar concentration of calcium chloride is in a range of between about 0.5 M and about 5.0 M. In a particular embodiment, the molar concentration of calcium chloride is in a range of between about 1.5 M and about 2.5 M.

In another embodiment, the temperature of the aqueous solution is in a range of between about 5° C. and about 95° C. In a specific embodiment the temperature of the aqueous solution is between about 20° C. and about 40° C.

In one particular embodiment, the aqueous solution is a carbonic anhydrase concentration of about 1 μmol, calcium chloride concentration of about 2 mol, a temperature of about 20° C., and a pH of about 8.0.

In yet another embodiment, the reaction is conducted in the presence of the cement surface for a period of time in a range of between about five minutes and about five days. In a specific embodiment the reaction is conducted in the presence of the cement surface for a period of time in a range of between about two minutes and about 24 hours.

Exemplification

The following is exemplification of the various embodiments of the invention. The various exemplified embodiments are not intended to be limiting in any way.

Materials and Methods

Enzyme.

Recombinant *Bos taurus* (cattle) CA-II expressed in *Escherichia coli* was purchased from Sigma Aldrich. The enzyme was dissolved in 0.1M Tris buffer, 160 mM NaCl, pH 9.5, aliquoted and stored at −20° C. until use.

Preparation of Cement Samples.

Small scale cement paste samples (10 mm diameter and 3 mm thick) were produced by first casting in a silicone mold, cast from a 3D printed part. The bottom surface of each mold had a corrugated surface of an approximate amplitude 0.2 mm and a frequency of 0.4 mm. The top surface of cement samples after casting were troweled to a smooth finish. The cement mix for the samples was prepared beforehand using a water to cement ratio of 0.4:1 by weight. The Portland cement batch (QUIKRETE® Portland Cement) was purchased from Home Depot and used for the entire study. The cement was cured in controlled conditions at ambient temperature for up to 2 months before use, in a saturated atmosphere steam room at 20° C. Each cement paste sample was split in half, so the final specimens had a fractured surface, a smooth top surface, and a ridged bottom surface.

Preparation of Perforated Cement Paste Slabs.

Thin cement paste slabs were manufactured in a similar manner to the samples. Silicone molds were made from 3D printed parts to create 50×50 mm square slabs 5 mm thick. Each slab was manufactured with nine circular perforations of diameter varying from 0.5 mm to 4 mm, simulating flaws of varying sizes. A cement paste mix with a water to cement ratio of 0.4 was used to cast these thin slabs, then cured in the steam room for at least seven days.

Preparation of Cement Paste Cubes.

Cement paste cubes of size 25 mm were manufactured in silicone molds made from a 3D printed part. Several cubes were made, the first a solid cube for control experiments. Two other cube types were made with through-holes cast in of two shapes, a 4 mm diameter circle and a 10×5 mm ellipse, simulating two flaw shapes. A cement paste mix with a water to cement ratio of 0.4 was used to cast these small cubes, then cured in the steam room for at least seven days.

Enzyme-Catalyzed Cement Healing.

The enzyme product was precipitated from a 49.6:49.6:0.74:0.0001 volume percent solution of four parts in a beaker on a stir plate: 200 mL of 2M calcium chloride dihydrate, 200 mL of 0.1M Tris base, ultrapure water, and a 5 μL aliquot of 20 mM bovine CA supplied in 150 mM sodium chloride. Thus, the amount of CA used was very small, and since it is a catalyst, recycles through millions of rounds of production. The primary 50:50 percent solution of 2M $CaCl_2$ and 0.1M Tris base had an initial pH of 9.5. The pH drops by 0.1 units upon addition of bubbled $CO_2$ gas. The 5 μL aliquot of the CA solution was rinsed from its container with 3 mL of ultrapure water and added to the beaker. Over the course of 20 minutes with continuous bubbling of $CO_2$ gas, the pH of the solution dropped from 9.5 to 7.4. The $CO_2$ gas treatment maintained a high level of $CO_2$ in solution as a material needed for the enzyme driven catalysis of $CaCO_3$.

The prepared cement paste samples were placed in the solution of CA, from which the calcium carbonate crystals precipitated. The solution was prepared in 1.5 mL vials, and then a specimen of cement paste was placed in each vial. Ultra-pure $CO_2$ gas was passed through the solution. Within a few minutes, a cloud of crystals in solution appeared due to CA catalysis of calcium chloride. During this time, the enzyme rapidly catalyzed the reaction of calcium chloride and $CO_2$ to produce calcium carbonate ($CaCO_3$) and carbon dioxide was the source of dissolved organic carbon.[3]

(1)

(2)

The vials were capped, and the samples kept in solution for 24 hours. Then, each vial was poured into a small aluminum dish. The specimens were taken out of the solution and placed in air. The samples were washed gently with water and placed in 50° C. oven for 24 hours to dry. Finally, the dried samples were thoroughly studied and imaged using optical and scanning electron microscopes.

Imaging.

Optical microscopy was performed with a Leica Upright Microscope DM LB2 with digital color imaging. SEM imaging was carried out on a FEI Quanta 200 FEG MKII, with both secondary electron (SE) and backscatter electron (BSE) imaging modes, at a voltage of 15 kV with a spot size of 3.0 nm and working distance of 9.5 mm. Samples were prepared in a carbon evaporator from a graphite source (Denton Vacuum 502-B). EDS analysis from an in-situ X-Ray spectrometer (Oxford Link Inca 350) within the SEM framework verified the composition and crystallography of the surface coating, with the processing option set as oxygen by stoichiometry (normalized).

In-situ XRD was carried out on a PANalytical Empyrean 2 X-ray Diffractometer, PANalytical B.V., Almelo, Netherlands), with a CuKα radiation source at 40 keV and 40 mA from 30 to 150 deg of 2θ.

FT-IR was carried out on a Bruker Optics Vertex 70 equipped with a Specac Golden Gate Diamond Single Reflection ATR element, Bruker, Billerica, Mass., USA.

Powder X-ray diffraction (pXRD) performed on a Bruker AXS D8 Focus, Bruker, Billerica, Mass., USA at 25° C. and pXRD spectrum used a CuKα radiation source at 40 keV and 40 mA from 20° to 90° of 2θ with a step size of 0.100°, against the baseline.

The perforations in the thin cement paste slabs and the flaws in the cubes were repaired with the enzyme product by funneling the solution directly into the simulated flaws. Following the prior described method of mixing the four-part solution and passing $CO_2$ gas through it, the CA enzymes catalyzed $CaCO_3$. Funnels were attached to the surface of the cement paste samples with silicone to ensure a watertight fit. The four-part solution was poured into the funnels and pooled into the flaws. The holes in the thin slabs were filled with $CaCO_3$ to the full slab thickness of 5 mm. The flaws in the cement paste cubes were filled with $CaCO_3$ to the full cube thickness of 25 mm. The four-part solution pooled in the flaws for 24 hours, after which any excess solution was extracted and the funnels removed. The repaired cement paste samples were then placed in a 50° C. oven for 24 hours to dry. The thin perforated slabs were then studied for the water-tightness of the repair, and the cubes were studied for uniaxial compressive strength.

Results

To confirm the hypothesis that enzymes can be a viable driving mechanism of crystal growth for repairing cracks and surface flaws in cementitious materials, the enzyme-driven coating was studied via numerous pathways after exposure to 0.1 μM of enzyme for 5 minutes followed by solution treatment for 12 hours on the surface of cement samples, followed by rinsing and then drying at 50° C. for 24 hours.

Figure 1A:
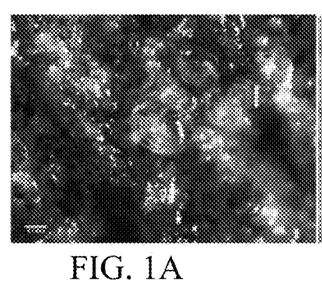
FIGS. 1A-1C are representative images of the enzyme product coating formed by one embodiment of the method of the invention. Data were taken from thirteen independent samples whose images showed similar surface crystals.
Figure 1B:
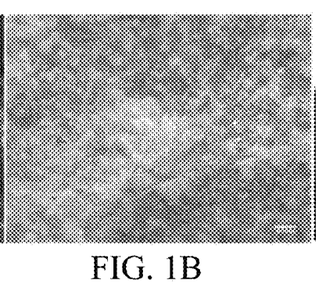
Figure 1C:
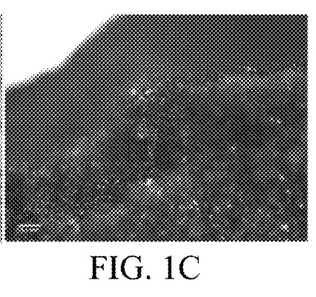

The evenness and adherence of the crystalline coating on the cement paste samples was studied via optical microscopy. Along the fractured edge of the cement paste sample, the crystal coating follows the contours of the specimen closely, (FIG. 1C). The normal size of the crystals in the coating was approximately 10 μm, and it was apparent that the fractured surface was not a challenge for the crystal coating because it closely followed the fracture patterns. In addition, the coating provided full coverage of the cement paste surface. Changing the viewing angle to across the surface revealed the apparent density of the crystals on the surface on the smooth, troweled top surface of the cement paste sample, (FIG. 1B). The color of the coating was clearly visible in this image and was a semi-transparent white. The grey cement paste substrate was still visible beneath. Further magnification revealed crystals of about 100 μm in diameter embedded in a semi-transparent film, shown at the center, (FIG. 1A). In the background of this third image, the grey-ridged surface of the cement paste sample was also visible, with corrugations of amplitude of 0.2 mm and a frequency of 0.4 mm. The surface roughness shown in this image was the negative impression of the mold used to create the samples. The dark grey background was the cured cement paste showing through the coating. From this round of digital color imaging it was apparent that the deposition of calcium carbonate onto the surface of the cement paste samples was not hindered by changes in the surface characteristics.

Figure 2A:
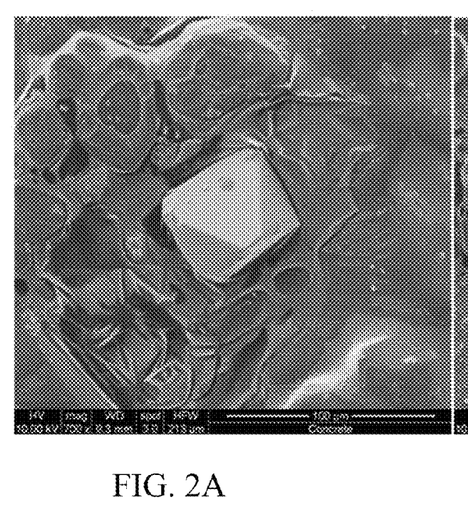
FIGS. 2A and 2B are both representative SEM color composite images of distinct $CaCO_3$ crystals of about 100 μm on the surface of a cement paste sample. The composite color imaging is made by combining secondary electron (SE) and backscatter electron (BSE) images, where the total number of samples is four and the total number of images is thirteen.
Figure 2B:
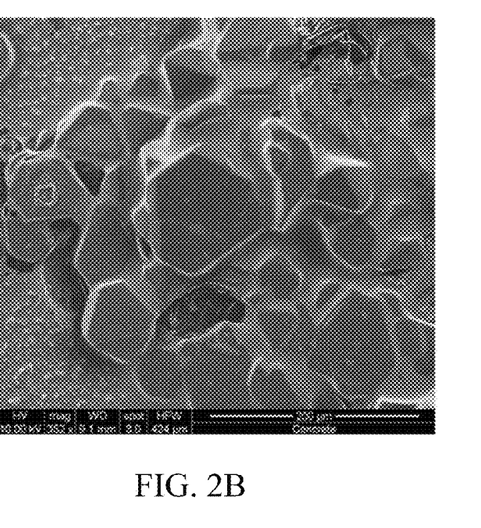

SEM imaging in both secondary electron (SE) and backscatter electron (BSE) modes was used characterize the surface morphology and chemical composition. The images in FIG. 2 are a color composite of the SE image and the BSE images showing both surface texture from the SE and relative atomic mass from the BSE. Overall, the surface morphology showed variable but distinct patterns of density in the surface treatment, with some clusters of crystals with varying density. FIG. 2A shows a 50 μm crystal on the cement paste surface in sharp white-blue color, which is clearly denser than the substrate and surrounding crystals. However, in FIG. 2B there is a cluster of crystals on the surface with little variation in density. The SEM images in FIG. 2 shows crystals of significant size that precipitated in a very short period (20 min), from 25 μm to 100 μm, on the surface of the cement paste.

Figure 3:
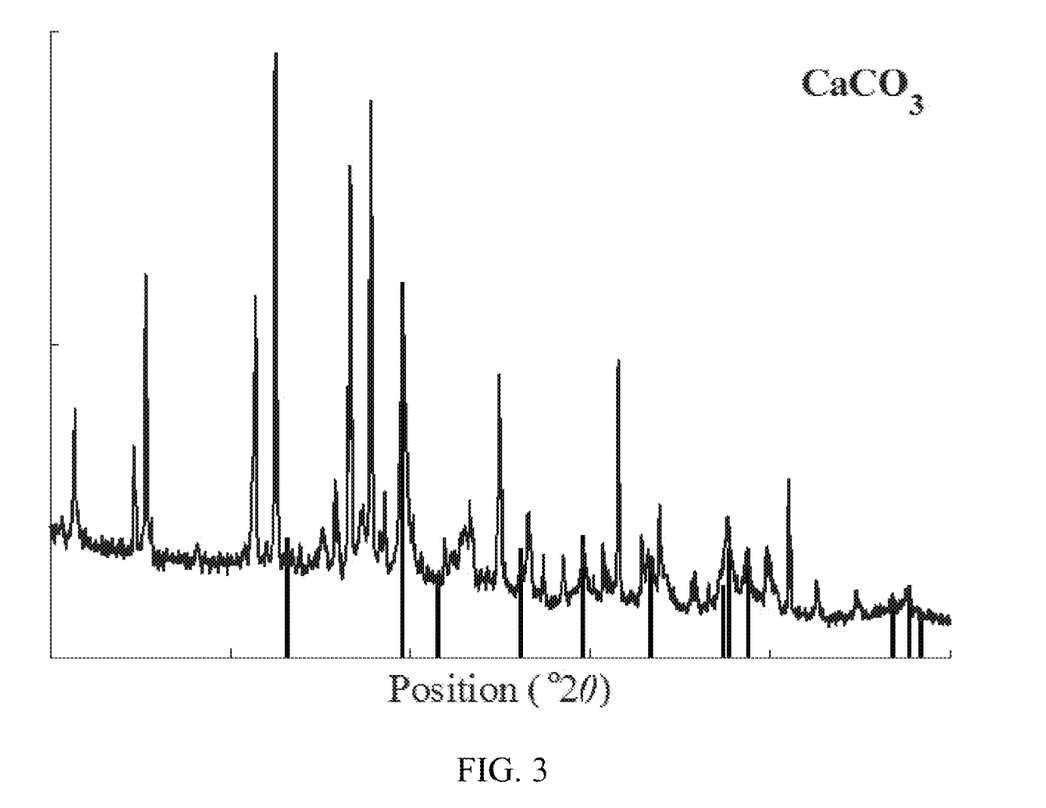
FIG. 3 is a plot of an XRD analysis of the surface of a cement paste sample coated by an embodiment of the method of the invention, and shows the presence of calcite peaks.

In-situ x-ray diffraction (XRD) was used to confirm the presence of the calcium carbonate coating as well as the calcium-silica-hydrate (C—S—H) cementitious substrate. XRD analysis on a coated cement paste sample showed the presence of both calcium (aluminum) silicate hydrate (C—S—H), the cement paste sample, and calcium carbonate crystals, $CaCO_3$. The strongest identified intensity match for calcium carbonate was the (104) plane at diffraction angle of 29.526°. The strongest identified intensity match for the cement paste substrate (C—S—H) was the (300) plane at diffraction angle of 26.666°. Results of the spectral analysis are shown in FIG. 3, where partial XRD patterns for the two identified phases, the crystalline $CaCO_3$ and the C—S—H substrate, are shown. The reference patterns are shown as bold black lines and the highest match is identified with nodal points.

Figure 4A:
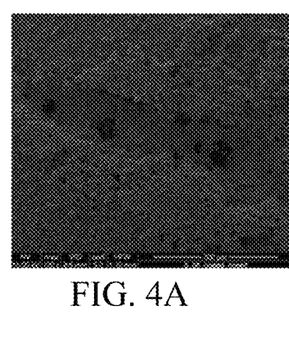
FIG. 4A is an optical microscopy image of a crack in the healing process using enzyme after 5 minutes treatment by enzyme and 12 hours in solution, n=7.
Figure 4B:
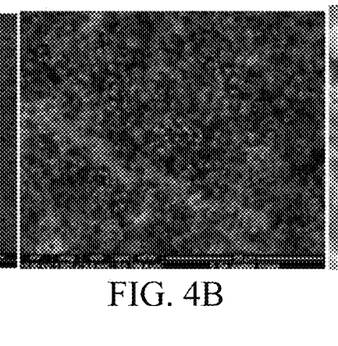
FIG. 4B is a scanning electron microscopy image of the same crack, n=6.
Figure 4C:
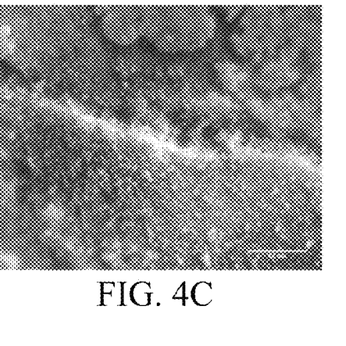
FIG. 4C is a higher resolution SEM image of the same crack, showing the presence of calcite crystals, n=6. All images show crystals. Composite color imaging was made by combining secondary electron and backscatter images.

The results of calcium carbonate crack-filling of a cement paste sample are shown in FIGS. 4A-4C. A cement paste sample was marked with a thin knife edge to create a surficial defect approximately 500 mm in length. The sample was treated with the enzyme solution for 5 minutes, and left in solution for 12 hours, rinsed, and dried at 50° C. for 24 hours. A defect that was approximately 0.2 mm wide and deep was partially filled within 5 minutes. Optical microscopy shows the white calcium carbonate crystals in the surface defect in FIG. 4A Successive SEM images with increasing magnification of the same location in the surficial defect are shown in FIG. 4B, middle and right. The presence of calcium carbonate crystals is clearly shown in the FIGS. 4B and 4C.

Figure 5:
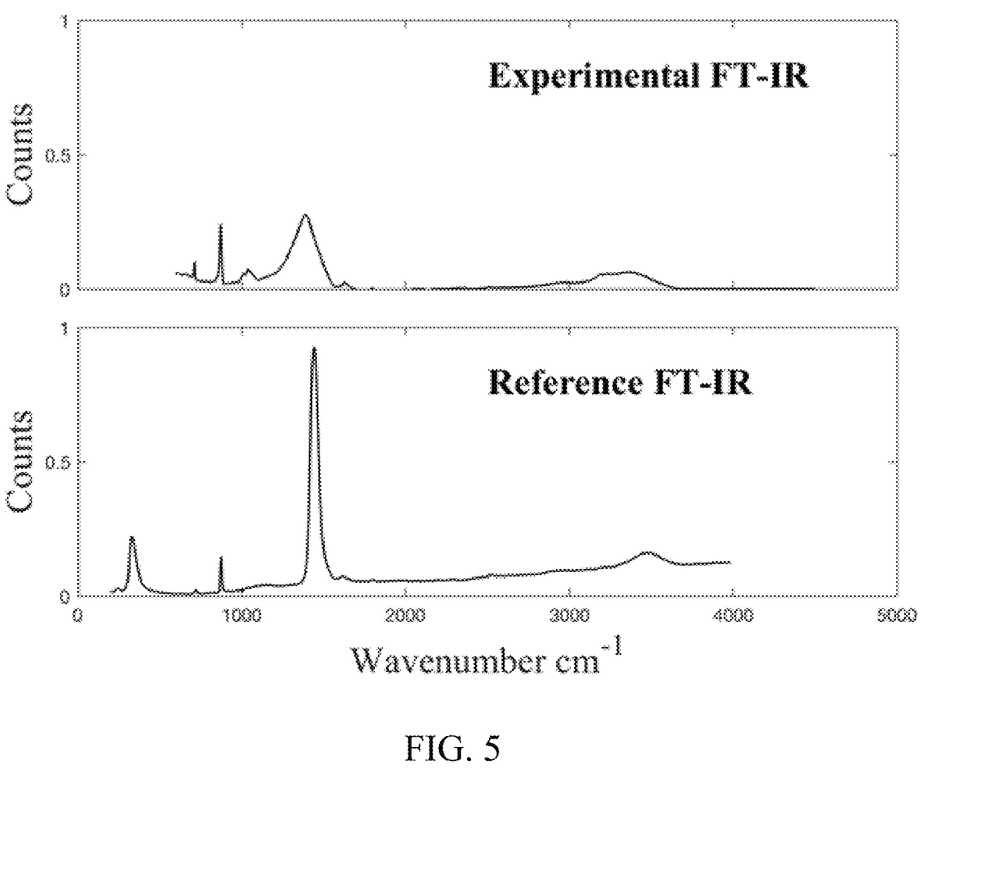
FIG. 5 shows plots of an FT-IR analysis of enzymatically-produced calcium carbonate formed by a method of the invention, with comparison to a reference spectrum where n=1 and the sample precipitate had a dry weight of 0.4 μg.
Figure 6:
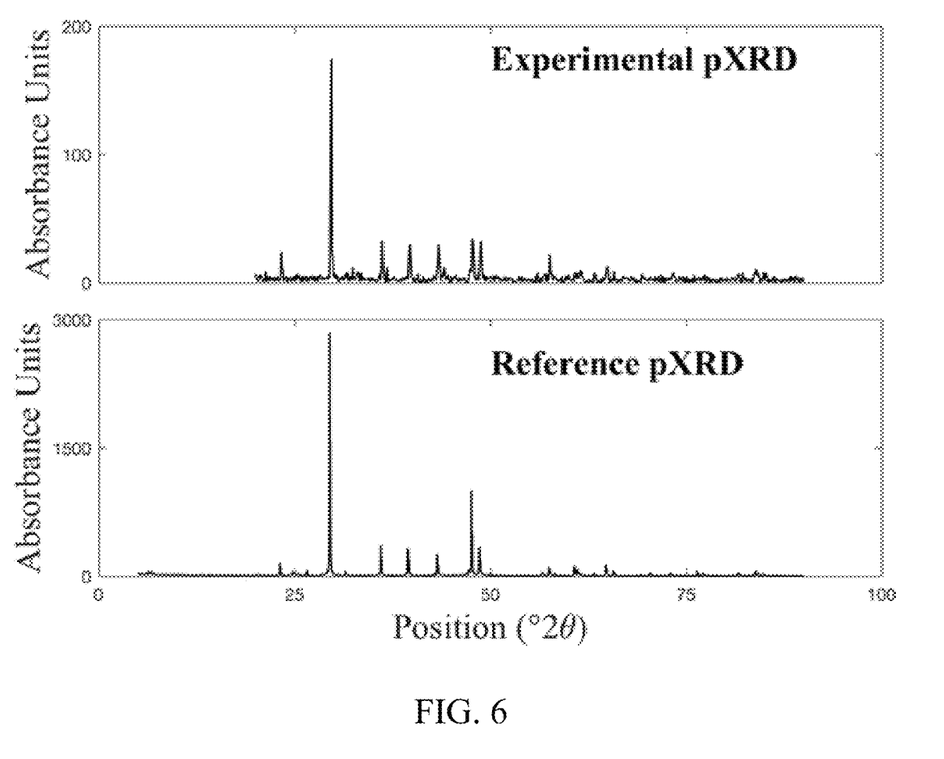
FIG. 6 shows plots of an pXRD analysis of enzymatically-produced calcium carbonate formed by a method of the invention, with comparison to a reference spectrum.

Analysis of the dried enzyme solution product was conducted by Fourier Transform Infrared Spectroscopy (FT-IR) and powder X-ray diffraction (pXRD) to confirm both the chemical composition and crystallinity. FIG. 5 compares the FT-IR spectrum of the dried enzyme product against the baseline FT-IR spectrum for calcium carbonate obtained from the RUFF Project database[4] and FIG. 6 compares the pXRD spectrum against the baseline. Both results verify the chemical composition and crystallinity of the enzyme product as calcium carbonate.

Figure 7:
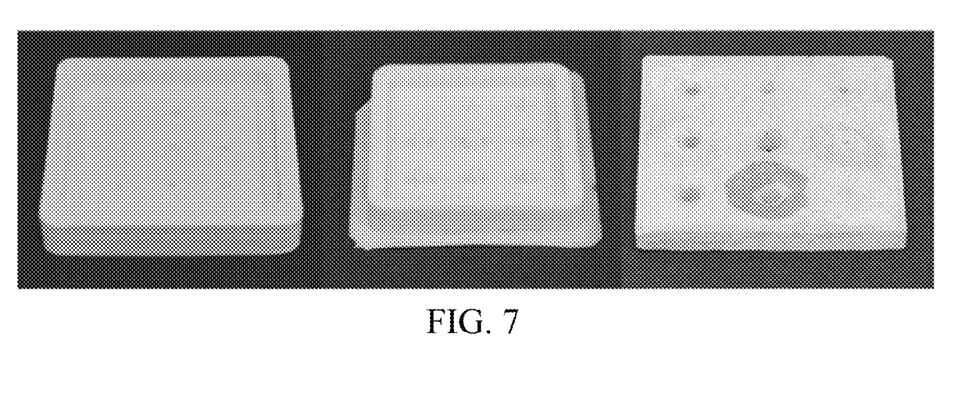
FIG. 7 is a photograph of a 3D printed mold (left) that was employed to form a silicone negative mold (middle) for a cement past slab (right).
Figure 8A:
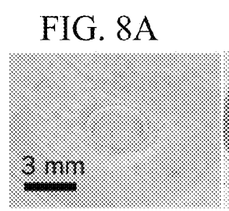
FIGS. 8A-8H are photographs of the results of filling holes in a thin cement paste slab with enzymatically produced calcium carbonate by a method of the invention. A 3 mm diameter hole (FIGS. 8A-8D) and a 4 mm diameter hole (FIGS. 8E-8H) are shown in a 5 mm thick cement paste slab. The holes were then plugged with the enzyme product (FIGS. 8B and 8F). Water-tightness was demonstrated, first with one or two drops of water (FIGS. 8C and 8G) and then with 10 drops of water (FIGS. 8D and 8H).
Figure 8B:
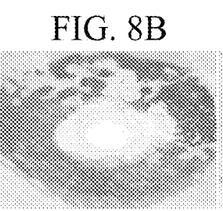
Figure 8C:
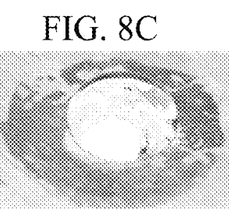
Figure 8D:
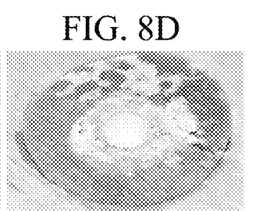
Figure 8E:
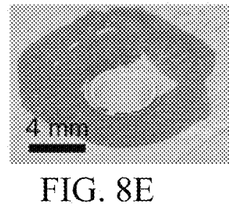
Figure 8F:
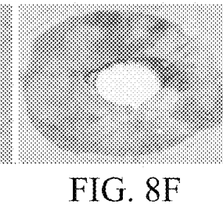
Figure 8G:
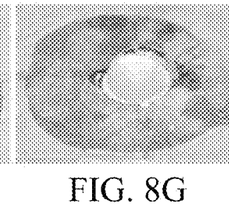
Figure 8H:
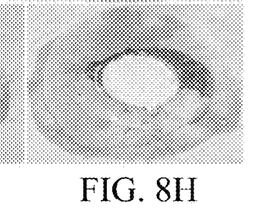

The feasibility of employing CA in solution to plug defects larger than a hairline crack by the method of the invention was tested on circular holes from 0.5 mm up to 4 mm in diameter in a 5-mm thin cement paste slab. Specifically, to create samples of slabs with appropriate hole diameters, a 3D printer was employed to construct a mold (FIG. 7), which was then employed to create a negative silicone mold of a sample having holes of appropriate diameter. Samples were cured for one week at 100% humidity and ambient temperature, and the holes were then plugged. A funnel system was created to channel the enzyme product as it settled out of solution into the holes. The holes were visibly plugged after the enzyme product settled out of solution in one day. The excess solution and funnel were then removed. At this point, the enzyme product was saturated and air dried at room temperature for one week. After thorough drying, the water-tightness of the plugged holes was tested by placing drops of ultrapure water over the holes, shown in FIGS. 8A through 8H. It was found that the enzyme product successfully held back 10 drops of water for the largest hole diameters of 3 mm in FIGS. 8A through 8D and 4 mm in FIGS. 8E through 8H.

Figure 9:
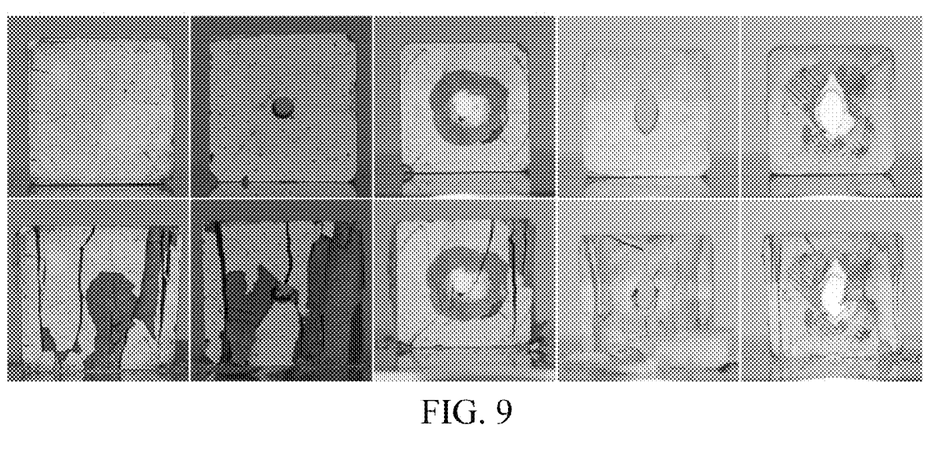
FIG. 9 is a series of photographs portraying, from left to right, the control samples, having a 4 mm circular flaw, a 4 mm circular flaw (repaired), a 5×10 mm vertical ellipse, and a 5×10 mm vertical ellipse (repaired).

Cubic samples of cement with two types of flaws were created for mechanical compressive testing. Using the same 3D printing and silicone mold manufacturing method described above for the slabs, three sets of 25 mm cubic samples were casted. The control sample was an intact 25 mm cube. The first flaw type was a 4-mm circular hole, which extended through the width of the cube sample. The second flaw type was a 10 mm by 5 mm vertically oriented elliptical flaw, that also extended completely through the width of the sample. The control and flawed samples are shown in FIG. 9 in the orientation used for compressive testing.

The flaws in a specific set of these samples were repaired using the method of the invention, then tested and compared to samples left unrepaired, as well as control samples. The results of compressive strength testing normalized to the control are presented in FIG. 10. The intact control samples were the baseline, and the enzymatically-repaired and unrepaired samples were compared. Repaired samples with a 4-mm circular flaw retained 90% of their original strength, while those left unrepaired retained 70% of their original strength (compared to the control sample). Repaired samples with a 10×5 $mm^2$ vertically-oriented elliptical flaw retained more than 80% of original, control strength, while those left unrepaired retained about 60% of the strength of the control samples.

Figure 10:
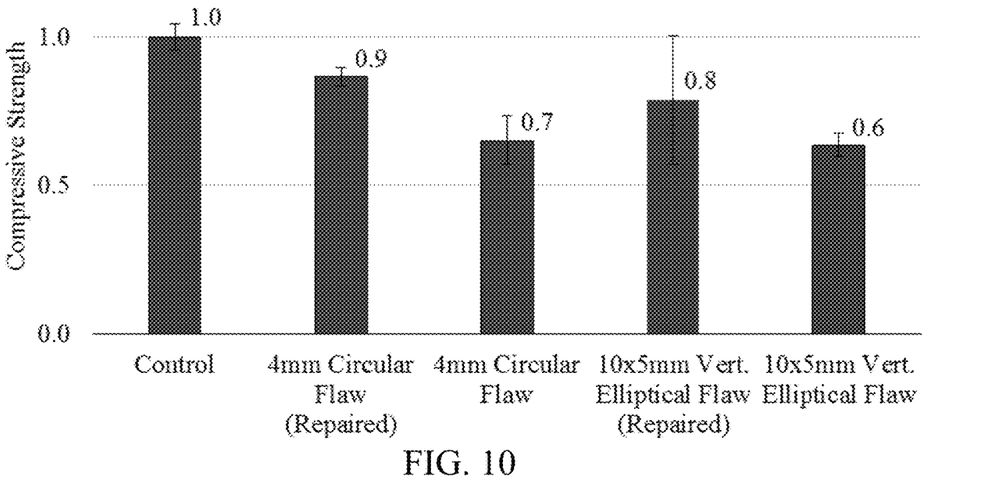
Figure 11:
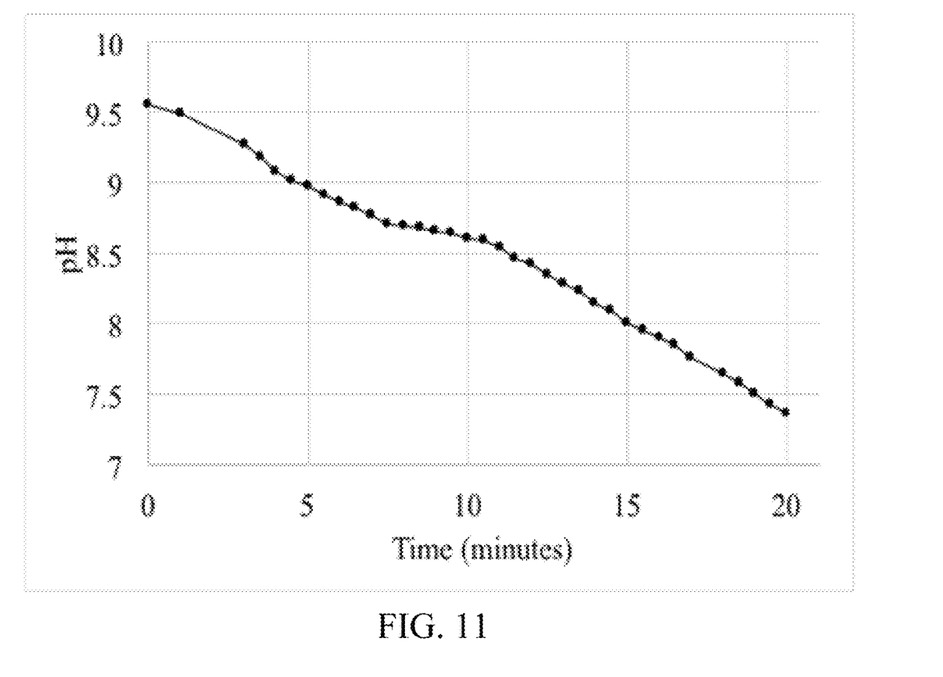
FIG. 11 is a plot of the pH over time of one embodiment of an enzyme solution employed by the method of the invention.

We tested the mechanical strengths of the repaired versus unrepaired samples (FIG. 8). The mechanical testing results clearly show that the samples with flaws can regain their original compressive strength using a very small amount of enzyme in a very short period of time. The large size of the healed flaws (~10 mm) exhibited the capability of the method of the invention to repair cement paste samples. Additionally, the fracture patterns of the cement paste samples in FIG. 10, showed the removal of stress concentrations around holes and cracks. Hence, the samples with relatively large circular holes (~4-5 mm in diameter) regained a significant portion of their original strength after the application of the CA enzyme solution by the method of the invention. The strength regained by cement paste samples with large elliptical holes, representing a relatively large crack, was slightly lower than that of the sample with a circular hole. This is believed to be due to the relatively large size of the cracks in these samples with respect to the size of the samples. Overall, the method of the invention demonstrated improvement in the mechanical properties presented in cement paste samples with different representations of large-size flaw geometries. The results also show that rapid crystal growth could be achieved by the method of the invention, whereas previous work employing bacterial enzymatic generation of $CaCO_3$, while improving compressive strength[6] of concrete having smaller flaw sizes occurred over a much longer time period.

Relatively small amounts of CA can be employed by the method of the invention to generate calcium carbonate precipitates that plug concrete flaws and holes having different geometries and, importantly, can significantly help the cement paste to regain compressive strength. These results of this research may have an immense impact beyond repairing concrete. Biological enzymes can be used in self-healing process for a variety of material systems requiring large and rapid production of crystals for repair. The possibilities in other engineering field are also endless as enzymes can help the repair of damaged ceramic parts.

While example embodiments have been particularly shown and described, it will be understood by those skilled in the art that various changes in form and details may be made therein without departing from the scope of the embodiments encompassed by the appended claims, such as by use of glass or ceramic as a substrate.

REFERENCES

1. Boden, T. A., Marland, G. & Andres, R. J. Global, Regional, and National Fossil-Fuel CO2 Emissions. (Oak Ridge National Laboratory, U.S. Department of Energy, Oak Ridge, Tenn., U.S.A., 2010).
2. Allen, R. T. L., Edwards, S. C. & Shaw, J. D. N. (Spon Press, Taylor & Francis Group, Abingdon, UK, 1993).
3. Li, W., et al. Calcium carbonate preciptation and crystal morphology induced by microbial carbonic anhydrase and other biological factors. Process Biochemistry 45, 1017-1021, doi:doi:10.1016/j.procbio.2010.03.004 (2010).
4. Lafuente, B., Downs, R. T., Yang, H. & Stone, N. (eds Thomas Armbruster & Rosa Micaela Danisi) 1-30 (W. De Gruyter, Berlin, Germany, 2015).
5. Jonkers, H. M., Thijssen, A., Muyzer, G. & Schlangen, E. Application of bacteria as self-healing agent for the development of sustainable concrete. Ecological Engineering 36, 230-235 (2010).

The relevant teachings of all patents, published applications and references cited herein are incorporated by reference in their entirety.

What is claimed is:

1. A method of sealing a cementitious surface comprising the step of physically contacting at least one opening or fissure of a cementitious surface with an aqueous solution of carbonic anhydrase and calcium chloride, the aqueous solution is exposed to an ambient atmosphere that includes carbon dioxide, whereby calcium carbonate is formed by a chemical catalyzation process performed by the carbonic anhydrase using ambient carbon dioxide, and precipitates to thereby seal the opening or fissure.

2. The method of claim 1, wherein the pH of the aqueous solution is in a range of between about 3.0 and about 9.5.

3. The method of claim 2, wherein the pH is in a range of between about 6.5 and about 9.5.

4. The method of claim 1, wherein the molar concentration of carbonic anhydrase of the aqueous solution is in a range of between 0.5 µM and about 1 mM.

5. The method of claim 4, wherein the molar concentration of carbonic anhydrase of the aqueous solution is in a range of between about 1 µm and about 10 µM.

6. The method of claim 4, wherein the molar concentration of calcium chloride is in a range of between about 0.5 M and about 5 M.

7. The method of claim 6, wherein the molar concentration of calcium chloride is in a range of between about 1.5M and about 2.5M.

8. The method of claim 6, wherein the temperature of the aqueous solution is between about 5° C. and about 95° C.

9. The method of claim 8, wherein the temperature of the aqueous solution is between about 20° C. and about 40° C.

10. The method of claim 1, wherein the aqueous solution has a carbonic anhydrase concentration of about I µM, a calcium chloride concentration of about 2M, a temperature of about 20° C., and a pH of about 8.0.

* * * * *